(12) United States Patent
Zhou

(10) Patent No.: US 9,428,697 B2
(45) Date of Patent: Aug. 30, 2016

(54) METHOD FOR JOINT PRODUCTION OF LOW OCTANE NUMBER GASOLINE AND HIGH OCTANE NUMBER GASOLINE

(76) Inventor: Xiangjin Zhou, Beijing (CN)

(*) Notice: Subject to any disclaimer, the term of this patent is extended or adjusted under 35 U.S.C. 154(b) by 0 days.

(21) Appl. No.: 13/885,276

(22) PCT Filed: Nov. 15, 2011

(86) PCT No.: PCT/CN2011/001909
§ 371 (c)(1),
(2), (4) Date: May 14, 2013

(87) PCT Pub. No.: WO2012/065364
PCT Pub. Date: May 24, 2012

(65) Prior Publication Data
US 2013/0237739 A1    Sep. 12, 2013

(30) Foreign Application Priority Data
Nov. 15, 2010  (CN) .......................... 2010 1 0542892

(51) Int. Cl.
*C07C 9/15*  (2006.01)
*C07C 7/06*  (2006.01)
*C07C 9/21*  (2006.01)
(Continued)

(52) U.S. Cl.
CPC ... *C10G 7/00* (2013.01); *C07C 7/06* (2013.01); *C07C 7/12* (2013.01); *C10G 7/12* (2013.01); *C10L 1/04* (2013.01); *C10L 1/06* (2013.01); *C10L 1/08* (2013.01); *C10L 10/10* (2013.01); *C10G 2300/305* (2013.01);
(Continued)

(58) Field of Classification Search
None
See application file for complete search history.

(56) References Cited

U.S. PATENT DOCUMENTS

| 4,975,178 A | 12/1990 | Clem et al. |
| 6,552,242 B1 | 4/2003 | Rice |

(Continued)

FOREIGN PATENT DOCUMENTS

| CN | 1074927 | 8/1993 |
| CN | 1710030 | 12/2005 |

(Continued)

OTHER PUBLICATIONS

Int'l Search Report for PCT/CN2011/001909, all pages, mailed Feb. 23, 2012.

(Continued)

*Primary Examiner* — Tam M Nguyen
(74) *Attorney, Agent, or Firm* — IPro, PLLC; Na Xu; Qian Gu (57) ABSTRACT

The present invention relates to a method for joint production of low octane gasoline and high octane gasoline. In the process of oil or light oil rectification, the extraction points of the distillates therein are finely divided, and the temperature ranges for extraction of fractions are narrowed down. Each of the low and high octane components having a high content in the range from C6-C12 (which may be extended to C5-C14 where necessary) is then separately extracted. After that, low octane components are combined into compression ignition low octane gasoline products, while high octane components are combined into high octane gasoline products. The remaining fractions are respectively added as supplementing agents into the low octane gasoline products or high octane gasoline products dependent on their octane ratings. Low octane gasoline is used in compression ignition gasoline engines, while high octane gasoline is used in spark ignition gasoline engines.

15 Claims, 3 Drawing Sheets

(51) Int. Cl.
    *C10G 7/00*     (2006.01)
    *C10L 1/06*     (2006.01)
    *C10L 1/08*     (2006.01)
    *C10L 10/10*     (2006.01)
    *C07C 7/12*     (2006.01)
    *C10L 1/04*     (2006.01)
    *C10G 7/12*     (2006.01)

(52) U.S. Cl.
    CPC ...... *C10G 2400/02* (2013.01); *C10L 2270/023* (2013.01); *C10L 2270/026* (2013.01); *C10L 2290/543* (2013.01)

(56) References Cited

U.S. PATENT DOCUMENTS

| | | | |
|---|---|---|---|
| 7,029,571 B1* | 4/2006 | Bhattacharyya et al. | 208/76 |
| 2003/0019789 A1* | 1/2003 | Kwak | 208/85 |
| 2006/0191820 A1* | 8/2006 | Mo et al. | 208/120.1 |
| 2010/0154117 A1* | 6/2010 | Odashima et al. | 5/87.1 |
| 2012/0271083 A1* | 10/2012 | Seames et al. | 585/322 |

FOREIGN PATENT DOCUMENTS

| | | |
|---|---|---|
| CN | 101134703 | 3/2008 |
| CN | 101475826 | 7/2009 |
| EP | 0553931 | 1/1993 |
| RU | 2043388 | 9/1995 |
| RU | 2102432 | 1/1998 |
| RU | 2106392 | 3/1998 |
| RU | 2113453 | 6/1998 |

OTHER PUBLICATIONS

Lin, *Petroleum Refining Engineering, 2nd Ed.*, Petroleum Industry Press, vol. 1, pp. 132-139 and 221-224 (Sep. 1994).
Int'l Preliminary Report on Patentability for PCT/CN2011/001909, all pages, mailed May 21, 2013.
EU search report, Nov. 3, 2014.
PUA—Office Action on Appl 5266/3A/15, Mar. 12, 2015.

* cited by examiner

METHOD FOR JOINT PRODUCTION OF LOW OCTANE NUMBER GASOLINE AND HIGH OCTANE NUMBER GASOLINE

This application is the U.S. national phase of International Application No. PCT/CN2011/001909, filed 15 Nov. 2011, which designated the U.S. and claims priority to Chinese Application No. 201010542892.X, filed 15 Nov. 2010; the entire contents of each of which are hereby incorporated by reference.

TECHNICAL FIELD

The present invention relates to the technical field of oil refining.

TECHNICAL BACKGROUND

1. The Compression Ratio and Thermal Efficiency of Engines

The compression ratio refers to the ratio of the largest volume of the gas and the smallest volume of the gas that can be obtained in the cylinder during the movement of the piston. When the piston is at the bottom of its stroke in the cylinder, the gas therein has the largest volume; when the piston is at the top of its stroke in the cylinder, the gas therein has the smallest volume. The former is called the total volume of the cylinder, while the latter is called the combustion chamber volume of the cylinder. The compression ratio equals the total volume of the cylinder divided by the combustion chamber volume. The compression ratio is an important indicator of an internal combustion engine, wherein a larger compression ratio would result in a larger cylinder pressure and a higher temperature.

Theoretically speaking, the higher the compression ratio is, the higher the efficiency of an engine will be.

The compression ratio of a gasoline engine is usually 4-6. The compression ratio of the gasoline engine of a passenger car is increased to 7-9.5 in order to acquire a higher volume/power ratio. The compression ratio of the gasoline engine of a high-end passenger car is said to have reached 12.5. High octane (high grade) gasoline shall be used in a gasoline engine with a high compression ratio. Otherwise, spontaneous combustion would arise in the cylinder during the movement of the engine, such that a knocking would be caused therein.

The compression ratio of a diesel engine is usually 15-18, such that the thermal efficiency of a diesel engine is 30% higher than that of a gasoline engine. The greenhouse effect brought about by the emission of a diesel engine is 45% lower than that by a gasoline engine. The emission of carbon monoxide and hydrocarbons of a diesel engine is also lower than that of a gasoline engine. A diesel engine adopts compression ignition. Therefore, no knocking problems exist therein. The compression ratio of a diesel engine cannot be too large though, due to limitation of the strength of material.

2. The Octane Rating and Knocking of Gasoline

Regular gasoline types (research) in the market include unleaded gasoline 90#, 93#, 95#, 97# and 98#. Gasoline 100# is said to exist in some places. The so-called 90#, 93# and 97# are content indicators of "octane rating" of the corresponding gasoline, respectively equivalent to 90%, 93% and 97% of "isooctane" highly capable of anti-knocking and 10%, 7% and 3% of "n-heptane" poor of anti-knocking. Therefore, the octane rating of the gasoline required by an engine becomes an indicator of the anti-knocking capability of the gasoline engine. If gasoline 90# is used where gasoline 97# is required, it would easily bring about a knocking.

Two methods are usually adopted in evaluating the anti-knocking property of fuel oil, namely motor octane rating and research octane rating. When the motor octane rating of fuel oil is 85, its research octane rating should be 92; when the motor octane rating is 90, its research octane rating should be 97. The octane ratings in this disclosure are all research octane ratings.

A regular type of gasoline has an octane rating larger than 90 and a relatively high ignition temperature, such that it cannot be normally ignited by compression ignition. Therefore, the gasoline engines nowadays are all spark ignition engines.

In order to improve the thermal efficiency of a gasoline engine and to avoid a knocking, gasoline producers are trying every means to increase the octane rating of gasoline. Therefore, the production of gasoline is increasingly complex and costly.

3. Low Octane Gasoline

In order to further improve the compression ratio, thus to improve the efficiency of gasoline engines, the concepts of low octane gasoline and compression ignition low octane gasoline engines are proposed. The operation principle of compression ignition low octane gasoline engines is similar with that of diesel engines. When low octane gasoline is sprayed into the compressed air having a high temperature and a high pressure in the cylinder, ignition and combustion automatically arise therein. Compression ignition low octane gasoline engines may have a higher compression ratio and therefore, a higher thermal efficiency and a smaller greenhouse effect than spark ignition engines.

Low octane gasoline is defined in the same manner as high octane gasoline. Low octane gasoline graded as gasoline 40#, 30# or 20# respectively comprises 40%, 30% or 20% of "isooctane" having high anti-knocking capability and 60%, 70% or 80% of "n-heptane" having low anti-knocking capability. Low octane gasoline can be graded as gasoline 42#, 33#, 0# or −10#, etc. as required.

Low octane gasoline is characterized by two aspects. On the one hand, compared with the currently used gasoline, this new low octane gasoline is capable of compression ignition. On the other hand, the fractions of this new low octane gasoline are close or similar to those of the currently used gasoline, which are generally in the range of C7-C11 and can be extended to C6-C12 or even C5-C19 when required.

For the sake of convenient distinction, in this description, gasoline with the octane rating lower than 50 is referred to as low octane gasoline and that with the octane rating higher than 90 (commonly used at present) is referred to as high octane gasoline.

4. Low Octane Gasoline Engines

Low octane gasoline engines have the advantages of both diesel engines and gasoline engines. Especially when the compression ratio is selected as within the range of 10-15, low octane gasoline engines have the advantages of gasoline engines as "a small size, small vibration and stable operation", and the advantages of diesel engines as "high efficiency, high power and a small greenhouse effect resulted by emissions".

With respect to compression ignition gasoline engines, a smaller octane rating of the gasoline may require a smaller compression ratio (ranging from 10-15, or 7-22) and lower mechanical strength, and lead to a lighter and handier structure and more gently and smoother operation. Generally speaking, even when the compression ratio of a compression ignition low octane gasoline engine is a very low, it should be still higher than the ratio of a spark ignition gasoline engine.

Therefore, a compression ignition low octane gasoline engine has higher thermal efficiency and a small green house effect resulted from emissions.

Low octane gasoline has shorter carbon chains and is more easily to burn. Therefore, there are few black granular impurities (black smoke) in the exhaust of a low octane gasoline engine. Tests have proved that when low octane gasoline is applied in an engine with the compression ratio of 18, there will hardly be any black smoke in the exhaust.

The corresponding minimum compression ratios of low octane gasoline of different octane ratings can be obtained by conventional experimental methods (the methods of measuring octane ratings) which are familiar to one skilled in the art.

5. Table 1 Shows the Octane Ratings and Boiling Points of Some Hydrocarbons.

TABLE 1

The relation between hydrocarbon structures and octane ratings and boiling points

| Name | Chemical formula | Boiling point (° C.) | Octane rating |
|---|---|---|---|
| n-tetradecane | $CH_3-(CH_2)_{12}-CH_3$ | 252-254 | <-45 |
| n-tridecane | $CH_3-(CH_2)_{11}-CH_3$ | 234 | <-45 |
| n-dodecane | $CH_3-(CH_2)_{10}-CH_3$ | 216.3 | <-45 |
| n-undecane | $CH_3-(CH_2)_9-CH_3$ | 196 | <-45 |
| n-decane | $CH_3-(CH_2)_8-CH_3$ | 174 | <-45 |
| nonane | $CH_3-(CH_2)_7-CH_3$ | 150.8 | -45 |
| n-octane | $CH_3-(CH_2)_6-CH_3$ | 125.7 | -17 |
| n-heptane | $CH_3-(CH_2)_5-CH_3$ | 98.5 | 0 |
| n-hexane | $CH_3-(CH_2)_4-CH_3$ | 68.7 | 25 |
| octene-1 | $CH_2=CH-(CH_2)_5-CH_3$ | 121.3 | 34.7 |
| ethylcyclohexane | $CH_3-CH_2-(C_6H_{11})$ | 131.8 | 44 |
| pentane | $CH_3-(CH_2)_3-CH_3$ | 36 | 61 |
| 1,1-dimethylcyclohexane | $CH_3-(C_6H_{10})-CH_3$ | 119.5 | 62 |
| octene-4 | $CH_3-(CH_2)_2-CH=CH-(CH_2)_2-CH_3$ | | 74.3 |
| cyclohexane | $C_6H_{12}$ | 80.2 | 77 |
| hexene-1 | $CH_2=CH-(CH_2)_3-CH_3$ | 63.3 | 80 |
| ethylbenzene | $C_6H_5-C_2H_5$ | 136.2 | 98 |
| isooctane | $(CH_3)_3C-CH_2-CH(CH_3)_2$ | 99.2 | 100 |
| dimethylbenzene | $CH_3-(C_6H_4)-CH_3$ | 138.35-144.42 | 103 |
| methylbenzene | $C_6H_5-CH_3$ | 110.6 | 104 |
| benzene | $C_6H_6$ | 80.1 | 108 |

6. Oil Refining

Crude oil is a black liquid, known as oil. This liquid contains aliphatic hydrocarbons, or hydrocarbons consisting of only hydrogen and carbon, wherein carbon atoms are linked together to form carbon chains of different lengths.

Currently, the process of oil refining mainly includes atmospheric distillation, reduced pressure distillation, hydrocracking, catalytic cracking, residual oil cracking, etc., wherein the light components of oil (light oil) are distilled off and the heavy components (long-chain alkanes and long-chain unsaturated hydrocarbons) are first converted into light components and then distilled off. In the distillation of light components, gasoline, aviation gasoline (aviation kerosene), kerosene and diesel are extracted in different stages based on the different condensation points or actually the different boiling points of each component of the light oil. The raw material for chemical products, i.e., "chemical light oil", also known as "naphtha" can also be extracted within a certain condensation point range according to the different functions of the light oil.

Figure 1:
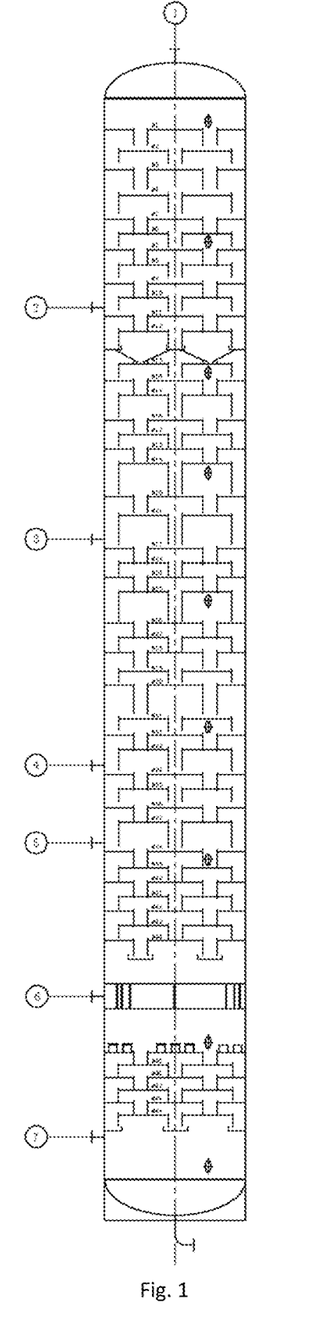
FIG. 1 is a schematic diagram of a typical atmospheric distillation column in prior art.

FIG. 1 is a schematic diagram of a typical atmospheric distillation column, in which, ① represents an outlet for gas hydrocarbons (comprising dry gas and liquefied petroleum gas, C1-C4), ② represents an outlet for gasoline (or called naphtha, C6-C11, or C5-C12), ③ represents an outlet for kerosene, ④ represents an outlet for diesel oil, ⑤ represents an outlet for heavy oil, ⑥ represents an inlet for heated crude oil vapor, and ⑦ represents an inlet for stripped vapor. The typical atmospheric distillation column comprises 49 pieces (layers) of column plates, which are disposed in sequence from No. 1 to No. 49. When the atmospheric distillation column is used for oil (crude oil) refining, heated crude oil vapor enters the distillation column via ⑥. The components of the crude oil disperse to different column plates, the top, and the bottom of the column, based on the boiling points thereof. The temperature at the top of the distillation column is low, while that at the bottom of the distillation column is high. Through heat exchange, the temperature at each layer of column plate is relatively stable. To facilitate the dispersion, a small amount of stripped vapor is introduced via ⑦, so that the oil vapor in the distillation column can uniformly disperse to corresponding column plates in accordance with its molecular structure, boiling point and dew point.

To improve the octane rating of gasoline, oil refining processes further comprise reforming, catalytic cracking, etc., wherein straight-chain paraffins with low octane ratings are converted into aromatics with high octane ratings. The light oil obtained by these processes also needs to be treated through the process of distillation or rectification, wherein gasoline, kerosene and diesel are respectively extracted in different stages based on their different condensation points.

7. The Innovative Methods of the Present Invention

In the distillation process according to the prior art, the products of gasoline, kerosene, diesel, etc. are produced by extracting the corresponding components within different ranges of condensation temperatures. Generally, one fraction corresponds to one product. In the present invention, however, different components are respectively extracted by "fixed-point extraction" based on the octane rating of each of the light oil component. Dependent on the principle that one component corresponds to one fraction extraction point, the components of different structures are extracted separately. After that, the components with low octane ratings are combined to prepare low octane gasoline products and the components with high octane ratings are combined to prepare high octane gasoline products. This method has neither been applied in the industry nor been reported of any research so far.

SUMMARY OF THE INVENTION

I. Technical Measures

In the process of oil rectification or light oil (e.g. naphtha, reformate oil, oil generated from catalytic (hydrogenating) cracking, pyrolysis oil or aromatic raffinate oil) atmospheric distillation or reduced pressure distillation, the extraction points of the distillates are finely divided such that the temperature range of the fractions is narrowed down. Each of the low octane gasoline and high octane gasoline components having a high content from C6-C12 is extracted separately in the order of content. After that, the low octane rating components are combined into compression low octane gasoline products and high octane rating components are combined into high octane gasoline products. The remaining fractions from C6-C12 are added as supplementing agents into the low octane gasoline or high octane gasoline based on the octane ratings thereof "Components having a high content" refer to the first 30 components from the highest to the lowest content sequence or those whose content accounts for 90% of the oil.

Alternatively, the components from the range of C5-C12 are separately extracted to prepare low octane gasoline products or high octane gasoline products dependent on the octane ratings of these components and the octane rating of the target products. The low octane gasoline products and high octane gasoline products are respectively used as the fuel of compression gasoline engines and spark ignition gasoline engines.

Those components that are not main components and those fractions that are not separately extracted are also respectively added into low octane gasoline products or high octane gasoline products according to their octane ratings. Those components or fractions unsuitable to be used as gasoline components, e.g. olefins, alkynes and benzene, serve other functions.

Figure 2:
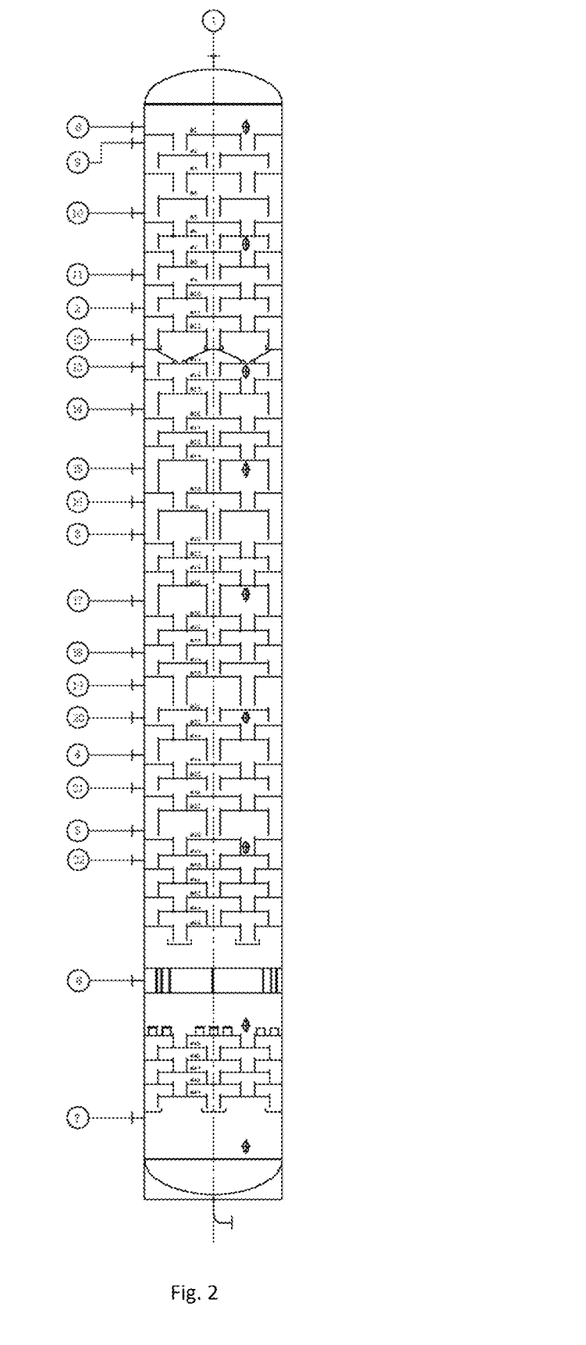
FIG. 2 is a schematic diagram of an atmospheric distillation column according to an embodiment of the invention.

FIG. 2 is a schematic diagram of an atmospheric distillation column of the invention, which is basically the same as that in FIG. 1 except that the atmospheric distillation column of the invention further comprises 15 product outlets ⑧-㉒. The original 49 pieces (layers) of column plates are disposed in the same manner as that in FIG. 1.

When the atmospheric distillation column as shown in FIG. 2 is used for oil (crude oil) refining, the joint production of low octanegasoline and high octane gasoline is achieved. The heated crude oil vapor enters the distillation column via ⑥, and the components of the crude oil disperse to different column plates, the top, and the bottom of the distillation column, based on the boiling points thereof. The temperature at each column plate is relatively stable. The introduction of a small amount of stripped vapor into the distillation column via ⑦ facilitates the dispersion of the oil vapor, so that the oil vapor in the distillation column can uniformly disperse to corresponding column plates in accordance with its molecular structure, boiling point and dew point. ① represents an outlet for gas hydrocarbons (comprising dry gas and liquefied petroleum gas), ⑥ represents an inlet for heated crude oil vapor, ⑦ represents an inlet for stripped vapor, and ②-⑤, and ⑧-⑫ are outlets for various distillate oil.

In FIG. 2, the components and concentrations of the oil in each plate column vary. Each column plate comprises a component having the largest concentration. By measurements, the components of the oil in each piece (layer) of column plate are clearly known. For example, based on the measurement results, the target products with the largest concentration from the nine outlets ② and ⑧-⑫ are listed in Table 2.

TABLE 2

Target products from different outlets and boiling points and octane ratings thereof

| Outlets | Name | Chemical formula | Boiling point ([deg.] C.) | Octane rating |
|---|---|---|---|---|
| ⑧ | pentane | CH3—(CH2)3—CH3 | 36 | 61 |
| | hexene-1 | CH2=CH—(CH2)3—CH3 | 63.3 | 80 |
| ⑨ | n-hexane | CH3—(CH2)4—CH3 | 68.7 | 25 |
| ⑩ | benzene | C6H6 | 80.1 | 108 |
| ⑩ | cyclohexane | C6H12 | 80.2 | 77 |
| ⑪ | n-heptane | CH3—(CH2)5—CH3 | 98.5 | 0 |
| ⑪ | isooctane | (CH3)3C—CH2—CH(CH3)2 | 99.2 | 100 |
| ② | methylbenzene | C6H5—CH3 | 110.6 | 104 |
| | 1,1-dimethyl-cyclohexane | CH3—(C6H10)—CH3 | 119.5 | 62 |
| | octene-1 | CH2=CH—(CH2)5—CH3 | 121.3 | 34.7 |
| ⑫ | n-octane | CH3—(CH2)6—CH3 | 125.7 | -17 |
| | ethylcyclohexane | CH3—CH2—(C6H11) | 131.8 | 44 |
| ⑬ | ethylbenzene | C6H5—C2H5 | 136.2 | 98 |
| ⑬ | dimethylbenzene | CH3—(C6H4)—CH3 | 138.35-144.42 | 103 |
| ⑭ | nonane | CH3—(CH2)7—CH3 | 150.8 | -45 |
| ⑮ | n-decane | CH3—(CH2)8—CH3 | 174 | <-45 |
| ⑮ | n-undecane | CH3—(CH2)9—CH3 | 196 | <-45 |
| | n-dodecane | CH3—(CH2)10—CH3 | 216.3 | <-45 |
| | n-tridecane | CH3—(CH2)11—CH3 | 234 | <-45 |
| | n-tetradecane | CH3—(CH2)12—CH3 | 252-254 | <-45 |

In Table 2, ⑬ ethylbenzene, ⑬ dimethylbenzene (mixed dimethylbenzene, comprising m-dimethylbenzene, p-dimethylbenzene, o-dimethylbenzene) and ② methylbenzene are high octane components, which are used for preparation of high octane gasoline and can also be used as chemical materials. High octane gasoline has an octane rating equal to or larger than 90 (RON). ⑨ n-hexane, ⑫ n-octane, ⑭ nonane, ⑬ n-decane, and ⑮ n-undecane are low octane components, which are used for preparation of low octane gasoline. Low octane gasoline has an octane rating equal to or smaller than 50 (RON). ⑩ benzene and ⑩ cyclohexane are used as chemical materials. ⑪ n-heptane and ⑪ isooctane are distilled off from the same outlet, which require for second separation. The separated n-heptane is added to low octane gasoline products, and the separated isooctane is added to high octane gasoline products.

In FIG. 2, after the distillate oil from the nine outlets ② and ⑧-⑮ are mixed, the resulting product has the same content as the gasoline (or called naphtha) from the outlet ② in FIG. 1. However, after separate extraction, each distillate oil of the nine distillate oil has different properties from the gasoline from the outlet ② in FIG. 1. The nine distillate oil has diverse utilization.

For example, in FIG. 2, ⑯ is an outlet for aviation kerosene No. 1, ③ is an outlet for aviation kerosene No. 3, ⑰ is an outlet for domestic kerosene. ⑱ and ⑲ are outlets for light diesel, and ⑳ and ④ are outlets for heavy diesel. ㉑, ⑤ and ㉒ are outlet for heavy oil.

When the octane rating of low octane gasoline is not low enough, low octane fractions of long carbon chains with more than 12 carbon atoms can be added to reduce the octane rating thereof. The octane ratings of paraffins with more than 12 or 13 carbon atoms are relatively low even when they are not straight-chain paraffins. Accordingly, it is an effective measure to add long-chain paraffins to reduce the octane rating of gasoline.

As to those components whose boiling points are close to each other (e.g. n-heptane and isooctane), and therefore cannot be simply separated through rectification, they can be extracted together as a mixture through rectification firstly, and then be further separated from each other through other means.

Obviously, the boiling points of the components that are added into low octane gasoline and high octane gasoline are discrete. Differently, in the rectification process of the prior art, diesel, kerosene, aviation kerosene and gasoline are successively extracted according to their temperatures in a descending order, wherein the boiling point temperatures within each product (fraction) is continuous.

The boiling point of pentane is 36° C. and the octane rating thereof is 61. Pentane generally does not serve as a component of gasoline (high octane gasoline). However, in the seasons when the temperature is low (e.g. winter or in the environment where the temperature is below 15° C.), as a low octane gasoline component, pentane can be added into low octane gasoline as a component of the new gasoline fuel. Hexane can also be used as the raw material to prepare low octane gasoline.

The present invention relates to a method for joint production of low octane gasoline and high octane gasoline, comprising the following steps:
(i) in the process of atmospheric distillation or reduced pressure distillation of crude oil, reformate oil, oil generated from catalytic cracking, oil generated from hydrogenating cracking, pyrolysis oil, or aromatic raffinate oil, separately extracting each of the components in the range from C5-C12 therein, or separately extracting each of the components having a high content therein in the order of content;
(ii) dependent on the octane ratings of the components obtained in step i) and the octane indexes of the target products, respectively using the components for preparing low octane gasoline or high octane gasoline products, which serve as the fuel for compression ignition engines or spark ignition engines respectively; and
(iii) alternately, suspending a plurality of small distillation columns outside the main distillation column in order to extract the components having a high content at fixed-points from the raw material, the temperatures at the top of the small columns respectively being controlled at the boiling points of the corresponding components, and the fractions in the small columns other than those required flowing back to the main column and being distilled off from other distillation ports of the main column.

In one example, the method comprises processing the components having a low content or other components that are not separately extracted from the raw material in the following steps:
(iv) respectively adding the components having a low content or other components that are not separately extracted from the raw material into low octane gasoline or high octane gasoline products in accordance with the octane numbers thereof;
(v) using components or fractions that are not suitable to serve as gasoline composition including olefins, alkynes, and benzene for other purposes; and
(vi) performing a second separation by other methods where necessary to separate the fractions that have close boiling points and therefore cannot be separated simply by the distillation method.

In another example, comprising processing a mixture of n-heptane and isooctane, the boiling points of which are close to each other, in the following steps:
(iv) extracting the mixture of n-heptane and isooctane by distillation;
(v) separating the mixture of n-heptane and isooctane obtained in step (iv) by adsorption separation, or by azeotropic distillation; and
(vi) adding n-heptane into low octane gasoline products or isooctane into high octane products respectively.

In some examples, in order to further reduce the octane rating of low octane gasoline, any component from long straight-chain alkanes can be added into the low octane gasoline, specifically comprising:
adding any component from C13-C14 straight-chain or non-straight-chain paraffins or any component from C13-C19 straight-chain or non-straight-chain paraffins into the low octane gasoline, namely adding components of kerosene or light diesel as additive for reducing the octane rating.

In a preferred example, the method comprises providing fraction extraction ports in high density on an oil or light oil distillation column in the following steps:
(iv) providing fraction extraction ports at an interval of 1° C. or 2° C. or 0.5° C. on the oil or light oil distillation column;
(v) collecting different fractions from the fraction extraction ports;
(vi) measuring or analyzing the light oil composition or octane rating of each fraction obtained in step (v);
(vii) using the fractions in the preparation of low octane gasoline or high octane gasoline products according to their octane ratings;
(viii) carrying our a second separation by other methods where necessary to separate complex fractions which comprise the mixture fraction of n-heptane and isooctane; and
(ix) providing fraction extraction ports at the temperature positions calculated to one decimal place on the distillation column for components with specific boiling points comprising a decimal place.

The present invention also relates to low octane gasoline and high octane gasoline products produced by using the method.

II. Technical Problems to be Solved

1. The problems of finely separating, separately distracting and selecting gasoline component are solved.
2. The problems of high energy consumption, high cost and lack of resources in producing high octane gasoline (gasoline 90# or that with a larger rating) currently are solved.
3. The problem that the octane rating of low octane gasoline is not low enough is solved.
4. The technical problem in separating n-heptane and isooctane is solved.
5. The problem that pentane or hexane cannot be used as gasoline fuel because of too low an octane rating is solved.

III. The Effects that are Brought about

1. Low octane gasoline can be obtained at a low cost, such that low-cost fuel can be provided to efficient, environmentally friendly and low-emission compression low octane gasoline engines.

Low octane components of gasoline have been a drag and burden to gasoline producers. However, it turns into a treasure now, because low octane gasoline is a low-cost, clean, environmentally friendly and high-quality fuel for internal combustion engines.

2. Not only low-cost low octane gasoline, but also low-cost high octane gasoline is obtained. The production process of gasoline is simplified, the raw material for producing gasoline becomes easier to obtain and the production structure becomes simpler and the cost lower.

For quite a long time, gasoline producers are trying to improve the octane ratings of gasoline, e.g. by the processes of reforming, catalytic cracking, etc., which has increased the cost and energy consumption in producing gasoline products. In order to improve the octane rating of gasoline, even antiknock agents such as MBTE, MMT, etc. are added into the gasoline, which decreases the environment friendliness of the gasoline products and increases harmful components in gasoline and the combustion exhaust thereof.

3. Compared with the prior art, the present invention can obtain high octane gasoline and low octane gasoline merely by separating the component of each fraction of the crude oil. The components need not to be converted from one to another such that the present invention provides a comparatively natural, simple, low-cost and environmentally friendly method.

DETAILED DESCRIPTION OF EMBODIMENTS

I. General Embodiments

1. The components of the raw material (oil or light oil) to be processed (distillation) are first of all analyzed and tested and then extracted respectively (separately) from the raw material according to their boiling points (as shown in Table 1) in the process of the distillation. The components are then combined in various manners (mixed) dependent upon their octane ratings and according to the octane rating indexes of the target products, wherein low-octane gasoline products and high octane gasoline products are respectively obtained. For example, dimethylbenzene, isooctane, ethylbenzene, hexene-1, etc. are used to prepare gasoline 97#, gasoline 93# or other high octane gasoline; n-undecane, n-decane, nonane, n-octane, n-heptane, n-hexane, octene-1, ethylcyclohexane, etc. are used to prepare gasoline 35#, gasoline 0# or other low octane gasoline; and cyclohexane, octene-4, 1,1-dimethylcyclohexane, etc. can be added into high octane or low octane gasoline as required or permitted.

Fixed-point extraction method: when 10 main components in the raw material for distillation are to be extracted by fixed-point extraction, 10 small distillation columns can be suspended outside the main distillation column, the temperatures at the top of the 10 small distillation columns being controlled as the boiling points of the corresponding components. Other distillates than those of the 10 components return to the main column and are distilled off from other ports thereof.

Figure 3:
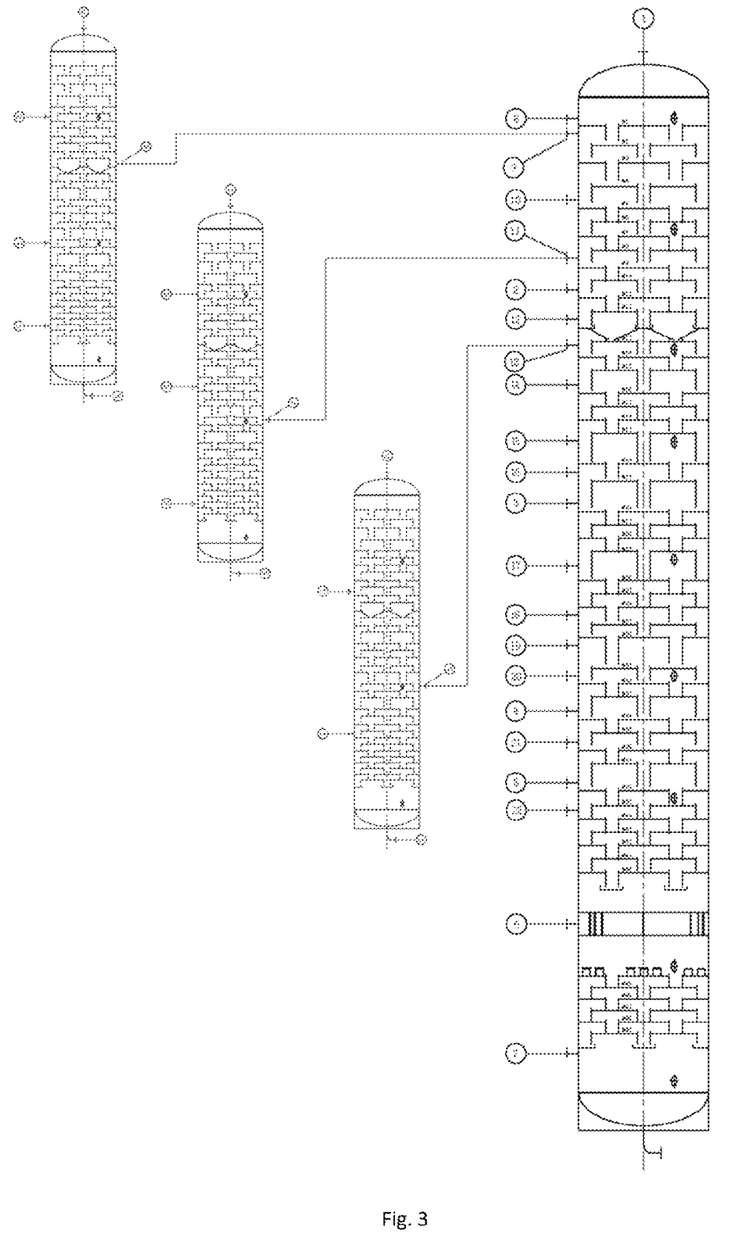
FIG. 3 is a schematic diagram showing three small distillation columns are suspended outside the main distillation column according to an embodiment of the invention.

FIG. 3 is a schematic diagram showing three small distillation columns are suspended outside the main distillation column, in which, the small distillation column a corresponds to the outlet ⑨ of the distillation column so as to enhance the concentration of the distillate from the outlet ⑨, the small distillation column b corresponds to the outlet ⑪ of the distillation column so as to enhance the concentration of the distillate from the outlet ⑪, the small distillation column c corresponds to the outlet ⑬ of the distillation column so as to enhance the concentration of the distillate from the outlet ⑬. As a result, the targeted extraction is achieved.

In another aspect, the nine outlets ② and ⑧-⑮ in FIG. 2 each can be equipped with a suspended small distillation column, so there are nine small distillation columns in total, which can enhance the concentration of target products of the nine distillate oil, respectively.

2. C12-C14 (or even longer-chain alkenes, such as C12-C14 alkenes) components can be added into low octane gasoline as required. In this case, the octane ratings of other components in the low octane gasoline can be appropriately increased, e.g. ethylcyclohexane, pentane, 1, 1-dimethylcyclohexane, and even octene-4 and cyclohexane can all serve as a component of low octane gasoline.

3. The components that are not listed out in Table 1 are respectively allocated and added into high octane gasoline or low octane gasoline dependent on the octane ratings of the components.

4. The Separation of n-Heptane and Isooctane:

Because the boiling points of n-heptane (98.5° C.) and isooctane (99.2° C.) are approximately close to each other, they are difficult to be separated by atmospheric distillation or reduced pressure distillation. In the present invention, these two components are first of all simultaneously extracted (e.g. by atmospheric distillation of the fractions in the range of 92-105° C.) and then separated by gas adsorption or azeotropic distillation. N-heptane is then used in the preparation of low octane gasoline and isooctane in the preparation of high octane gasoline.

In the industrial production, 5 A molecular sieves are usually adopted as an adsorbent of straight-chain paraffins such as n-heptane and steam is usually used as a desorbent, such that n-heptane can be extracted and separated from isooctane.

In the industrial production, methanol is usually adopted as an entrainer of n-heptane to separate and extract n-heptane, such that n-heptane and isooctane can be separated.

Currently, it is not known how to separate n-heptane and isooctane from each other in the oil refining industry. Therefore, the separation technique mentioned above is one of the innovations of the present invention.

Through separation of n-heptane and isooctane, a high octane component with the octane rating as 100 and a low octane component with the octane rating as 0 will be simultaneously obtained, which would be an important contribute to the joint production low octane gasoline and high octane gasoline of the present invention.

II. Simplified Embodiments

1. In order to reduce the complexity of the process of "fixed-point extraction" (separate extraction) from the light oil, some extraction points can be omitted according to the actual situation, such that the distillation fraction extraction points can be reduced, e.g. the number of the "components with a high content" can be reduced from 30 to 28, 24 or 20, etc.

2. The remaining fractions other than those which are extracted "separately" can be respectively extracted together with either of the two adjacent components in the extraction temperature sequence in accordance with the principle of proximity of octane ratings.

For example, among all the components in the range of C7-C11, suppose the content number of a component is 31, whose octane rating is 34.7 and whose boiling point is 121.3° C.; the extraction point and octane rating of its high temperature adjacent fraction are respectively 131.8° C. and 44, and those of its low temperature adjacent fraction are respectively 119.5° C. and 62. In this case, this component will be extracted together with the fraction whose extraction point is 131.8° C., because their octane ratings (respectively 34.7 and 44) are 9.3 points away from each other, which is smaller than the distance between 34.7 and 62 (i.e., 27.3).

3. Dimethylbenzene comprises three isomers, whose boiling points and octane ratings are close to one another, such that they can be extracted as a fraction and serve as a mixture component of high octane gasoline.

4. Dimethylbenzene and ethylbenzene can be extracted as a fraction and serve as a component of high octane gasoline.

5. Methylbenzene, dimethylbenzene and ethylbenzene can be extracted as a fraction and serve as a component of high octane gasoline.

6. Fraction extraction points are uniformly provided at a small interval on the distillation column of oil or light oil. For example, fraction extraction ports are provided at an interval of 1° C. (or 2° C., 0.5° C. or other temperatures) to collect the fractions of different condensation points. The light oil composition or octane rating of each fraction is tested (analyzed) and the fractions are used in the preparation of low octane gasoline or high octane gasoline or to serve other functions according to their octane ratings. As to fractions of complex compositions (e.g. the mixture fraction of n-heptane and isooctane), a secondary separation can be carried out by other methods where necessary. Although the above-mentioned method seems far from satisfactory and requires complex distillation equipment, it excels in simple production organization and good adaptability to different sources of raw materials.

For components with specific boiling points where a decimal place is included (e.g. the boiling point of 1, 1-dimethylcyclohexane is 119.5° C. and that of n-octane is 126.7° C.), fraction extraction points at the temperature positions calculated to one decimal place are provided on the distillation column (fraction collection points are provided respectively at the temperature positions of 119.5° C. and 126.7° C.).

As experience accumulated, most fractions can be transported through the pipeline directly to the low octane gasoline tank or the high octane gasoline tank.

7. As to the remaining portion after the process of rectification extraction (fixed-point extraction), it is divided into two parts dependent upon the boiling points of the fractions. Generally, fractions of high temperatures enter into low octane gasoline while fractions of low temperatures enter into high octane gasoline, which, however, is merely an empirical approach. Whether the fractions or how much of the fractions enter into the gasoline with corresponding octane ratings should be determined according to the test result of the octane ratings as actually required.

III. Supplementary Explanations

1. In producing high octane gasoline with the method of the present invention, anti-knock agents may not be added to the maximum extent. Generally speaking, it is neither economy nor environmentally friendly to add anti-knock agents into gasoline.

2. In this disclosure, only the technical solutions in producing high octane gasoline and low octane gasoline are provided. Where the issue of safety or environment protection is concerned with respect to the relevant components of gasoline products, the gasoline product standards of local authorities should be observed.

3. No creative work is involved in preparing different grades of gasoline with addition of fractions of different octane ratings.

4. The present invention does not exclude the method of adding ethanol or antiknock agents such as MBET, MMT, etc. in high octane gasoline products. On condition that the octane standard is measured up, low octane gasoline can be mixed with ethanol to serve as a mixture fuel.

5. In the rectification extraction methods such as "fixed-point extraction" or "separate extraction" recited in this disclosure, the extracted component may not be pure. However, this method is a success as long as most of the target component is extracted, and among the actually extracted components, the target component accounts for the most part. As the extraction techniques are improved, e.g. the theoretical increase of column plates and the increasingly narrowing of the boiling point range of the rectification extracts, the content of the target component (concentration) obtained by the present method (fixed-point extraction or separate extraction) in each extraction component will be increasingly high.

6. The pressure can be reduced or the theoretical column plates can be increased in order to separate n-heptane and isooctane.

7. A liquid adsorption method is adopted to separate isooctane and n-heptane. The liquid adsorption separation method is a frequently-used industrial production method, e.g. paraxylene (PX) is extracted from the mixture of dimethylbenzene mainly by this method. The design and production of an adsorbent belongs to a professional technical field, wherein the adsorbent required in the separation of n-heptane and isooctane can be conveniently provided. The adsorbent according to this method can be sued to adsorb either n-heptane or isooctane. The adsorbent technique itself is not included in the claims of the present invention.

The invention claimed is:

1. A method for joint production of low octane gasoline and high octane gasoline, comprising the following steps:
(i) in a process of atmospheric distillation or reduced pressure distillation of raw material which is crude oil, reformate oil, oil generated from catalytic cracking, oil generated from hydrogenating cracking, pyrolysis oil, or aromatic raffinate oil, each of the components with a high content from the range of C5-C12 therein is separately extracted, or each of the components having a main content therein is separately extracted in the order of content;
according to the number of said components having a main content to be extracted, the number of the exits for extracted distillates, the distillation outlets disposed in the distillation column is increased; with said components having a main content as targets, the column plate having a temperature close to boiling point with a target component is selected as the position of the distillation outlet for extracting the target component;
the temperature of the column plate is controlled based on the boiling point of the target component, to obtain a distillate or a mixture having a high content of the target component by extracting from said distillation outlet;
(ii) dependent on their octane ratings of the distillates obtained in step (i) and octane indexes of target products, deriving both low octane gasoline products and high octane gasoline products, serving as fuel for compression ignition gasoline engine and spark ignition gasoline engine respectively;

(iii) the distillation column is provided with at least one distillation outlet for distilling off other distillates not aimed at the target components.

2. The method according to claim 1, further comprising processing distillates having a low content or other distillates that are not separately extracted from the raw material in the following steps:
   (iv) respectively adding the distillates having a low content or other distillates that are not separately extracted from the raw material into low octane gasoline or high octane gasoline products in accordance with the octane numbers thereof;
   (v) using distillates or fractions that are not suitable to serve as gasoline composition including olefins, alkynes, and benzene for other purposes; and
   (vi) performing a second separation by other methods where necessary to separate the fractions that have close boiling points and therefore cannot be separated simply by the distillation method.

3. The method according to claim 1, wherein in order to further reduce the octane rating of low octane gasoline, any component from long straight-chain alkanes can be added into the low octane gasoline, namely adding components of kerosene or light diesel as additive for reducing the octane rating.

4. The method according to claim 1, further comprising processing a mixture of n-heptane and isooctane, the boiling points of which are close to each other, in the following steps:
   (iv) extracting the mixture of n-heptane and isooctane by distillation;
   (v) separating the mixture of n-heptane and isooctane obtained in step (iv) by adsorption separation; and
   (vi) adding n-heptane into low octane gasoline products or isooctane into high octane products respectively.

5. The method according to claim 1, further comprising processing a mixture of n-heptane and isooctane, the boiling points of which are close to each other, in the following steps:
   (iv) extracting the mixture of n-heptane and isooctane by distillation;
   (v) separating the mixture of n-heptane and isooctane obtained in step (iv) by azeotropic distillation; and
   (vi) adding n-heptane into low octane gasoline products or isooctane into high octane products respectively.

6. The method according to claim 3, wherein the component from long straight-chain alkanes is any component from C13-C14 straight-chain paraffins.

7. The method according to claim 3, wherein the component from long straight-chain alkanes is any component from C13-C19 straight-chain paraffins.

8. The method according to claim 3, wherein the component from long straight-chain alkanes is any component from C13-C14 or C13-C19 non-straight paraffins.

9. The method according to claim 1, further comprising providing fraction extraction ports at high density on an oil or light oil distillation column in the following steps:
   (iv) providing fraction extraction ports at an interval of 1° C. on the oil or light oil distillation column;
   (v) collecting different fractions from the fraction extraction ports;
   (vi) measuring or analyzing the light oil composition or octane rating of each fraction collected in step (v);
   (vii) using the fractions are used in preparation of low octane gasoline or high octane gasoline products according to their octane ratings;
   (viii) carrying out a second separation by other methods where necessary to separate complex fractions which comprise the mixture fraction of n-heptane and isooctane; and
   (ix) providing fraction extraction points at the temperature positions calculated to one decimal place are provided on the distillation column for components with specific boiling points comprising a decimal place.

10. The method according to claim 1, further comprising providing fraction extraction ports at high density on an oil or light oil distillation column in the following steps:
    (iv) providing fraction extraction ports at an interval of 2° C. on the oil or light oil distillation column;
    (v) collecting different fractions from the fraction extraction ports;
    (vi) measuring or analyzing the light oil composition or octane rating of each fraction collected in step (v);
    (vii) using the fractions are used in preparation of low octane gasoline or high octane gasoline products according to their octane ratings;
    (viii) carrying out a second separation by other methods where necessary to separate complex fractions which comprise the mixture fraction of n-heptane and isooctane; and
    (ix) providing fraction extraction points at the temperature positions calculated to one decimal place are provided on the distillation column for components with specific boiling points comprising a decimal place.

11. The method according to claim 1, further comprising providing fraction extraction ports at high density on an oil or light oil distillation column in the following steps:
    (iv) providing fraction extraction ports at an interval of 0.5° C. on the oil or light oil distillation column;
    (v) collecting different fractions from the fraction extraction ports;
    (vi) measuring or analyzing the light oil composition or octane rating of each fraction collected in step (v);
    (vii) using the fractions are used in preparation of low octane gasoline or high octane gasoline products according to their octane ratings;
    (viii) carrying out a second separation by other methods where necessary to separate complex fractions which comprise the mixture fraction of n-heptane and isooctane; and
    (ix) providing fraction extraction points at the temperature positions calculated to one decimal place are provided on the distillation column for components with specific boiling points comprising a decimal place.

12. The method according to claim 1, wherein each of components having a high content therein comprises the first 30 components from the highest to the lowest content sequence of the starting source.

13. The method according to claim 1, wherein each of components having a high content therein comprises components from the highest to the lowest content sequence whose contents combined accounts 5 to 90% of the starting source.

14. The method according to claim 1, wherein each of components having a high content therein comprises components in the range of C5-C12 of the starting source.

15. The method according to claim 1, wherein a plurality of small distillation columns are provided outside a main distillation column in order to further improve the concentrations of a plurality of the target components with a high content in the raw materials in the distillate, wherein a part of the distillation outlets of the main distillation column are connected with raw material inlets of the small distillation columns, namely, the distillate outlet for a distillate of a target component with a high content in the main distillation column is connected with the raw material inlet of the small distillation column for extracting the target component; the temperatures at the top plates of the small distillation columns are controlled respectively at the boiling points of the plurality of the target components; inside the small distillation columns, in addition to that the distillates having high content of the target components are extracted, all other distillates flow back into the main distillation column as raw materials of the main distillation column and distilled off from other distillation outlets of the main distillation column; and each of the small distillation columns are provided with at least one distillation outlet connected with the raw material inlet of the main distillation column.

* * * * *